(12) United States Patent
Taguchi et al.

(10) Patent No.: US 9,320,622 B2
(45) Date of Patent: Apr. 26, 2016

(54) NICKEL-FREE STAINLESS STEEL STENT

(75) Inventors: Tetsushi Taguchi, Tsukuba (JP);
Yasuyuki Katada, Tsukuba (JP); Ryozo Nagai, Tokyo (JP); Ichiro Manabe, Tokyo (JP); Katsuhito Fujiu, Tokyo (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 296 days.

(21) Appl. No.: 13/988,870

(22) PCT Filed: Nov. 25, 2011

(86) PCT No.: PCT/JP2011/077241
§ 371 (c)(1),
(2), (4) Date: Jul. 29, 2013

(87) PCT Pub. No.: WO2012/070659
PCT Pub. Date: May 31, 2012

(65) Prior Publication Data
US 2013/0304184 A1 Nov. 14, 2013

(30) Foreign Application Priority Data
Nov. 26, 2010 (JP) ................. 2010-264359

(51) Int. Cl.
| | |
|---|---|
| C22C 38/22 | (2006.01) |
| C22C 38/02 | (2006.01) |
| C22C 38/04 | (2006.01) |
| A61F 2/82 | (2013.01) |
| C22C 38/00 | (2006.01) |
| C22C 38/26 | (2006.01) |
| C22C 38/28 | (2006.01) |
| A61L 31/02 | (2006.01) |

(52) U.S. Cl.
CPC .................. *A61F 2/82* (2013.01); *A61L 31/022* (2013.01); *C22C 38/001* (2013.01); *C22C 38/002* (2013.01); *C22C 38/02* (2013.01); *C22C 38/04* (2013.01); *C22C 38/22* (2013.01); *C22C 38/26* (2013.01); *C22C 38/28* (2013.01)

(58) Field of Classification Search
None
See application file for complete search history.

(56) References Cited

U.S. PATENT DOCUMENTS

| | | | | |
|---|---|---|---|---|
| 6,682,582 | B1 * | 1/2004 | Speidel | B22F 1/0059 419/37 |
| 2006/0130934 | A1 | 6/2006 | Kuroda et al. | |
| 2007/0098588 | A1 * | 5/2007 | Narita | C22C 38/001 420/57 |
| 2007/0186999 | A1 | 8/2007 | Kuroda et al. | |

FOREIGN PATENT DOCUMENTS

| | | |
|---|---|---|
| JP | 2004-167045 | 6/2004 |
| JP | 2006-316338 | 11/2006 |

OTHER PUBLICATIONS

International Search Report issued Feb. 21, 2012 in corresponding International Application No. PCT/JP2011/077241.

* cited by examiner

*Primary Examiner* — Deborah Yee
(74) *Attorney, Agent, or Firm* — Wenderoth, Lind & Ponack, L.L.P.

(57) ABSTRACT

A nickel-free stainless steel stent using a stainless steel which does not substantially contain Ni in the stainless steel, has a metal allergy onset-preventing effect, and is excellent in terms of precision workability, strength, and ductility, is provided. The nickel-free stainless steel stent is characterized by using a stainless steel containing, as a chemical composition, from 15 to 30% by mass of Cr, from 0.97 to 2% by mass of Mo, and from 0.5 to 1% by mass of N, with the remainder being Fe, and optionally containing inevitable impurities.

22 Claims, 4 Drawing Sheets

23Cr-1Mo-1N 3 hrs     1 d     3 d

SUS316L 3 hrs     1 d     3 d

NICKEL-FREE STAINLESS STEEL STENT

TECHNICAL FIELD

The present invention relates to a nickel-free stainless steel stent. In detail, the present invention relates to a nickel-free stainless steel stent using a stainless steel which does not cause an allergic reaction in a human body and which is excellent in terms of precision workability, strength, and ductility.

BACKGROUND ART

A stent for vasodilatation is known as a medical instrument which is used for the therapy of expanding a stenosed portion of a blood vessel such as a coronary artery, etc. for patients with angina, myocardial infarction, or the like. This stent for vasodilatation is, for example, made of a metallic mesh that is expanded in a cylindrical state and is inserted into a diseased part such as a stenosed blood vessel, etc. with a catheter to expand the blood vessel.

Conventionally, an austenite-based stainless steel that is a general stainless steel, such as SUS316, etc., is used for a material of this stent for vasodilatation.

On the other hand, in recent years, attention is paid to an issue of metal allergy in a human body. This metal allergy is one in which a certain kind of metal constituting a metal material is ionized according to environmental conditions for use; the formed metal ion is bound to a protein within an epidermis, a mucosal epithelium, or a cell of the human body; a chemical material which the human body does not originally possess is formed; and the living cell causes a rejection reaction against this chemical material, leading to an abnormality in the human body. As one of metal elements causing the onset of such a disease of metal allergy, Ni (nickel) is known to be a causative material.

Under such circumstances, in view of the fact that in SUS316 that is used as the above-described material of a stent for vasodilatation, which is a general austenite-based stainless steel, from 10 to 14% by mass of Ni is contained, whereas in SUS316L, from 12 to 15% by mass of Ni is contained, there is a concern of the onset of metal allergy due to elution of an Ni ion after inserting the stent for vasodilatation into the blood vessel.

As described above, from the viewpoint that the presence of Ni in the metal material is a cause of the onset of metal allergy, in the stainless steels as metal materials which have been used so far for implants, stents for vasodilatation, or instruments for living body or medical treatment, accessories or garment parts used in a state of direct contact with the skin surface of the human body, and tablewares, a stainless steel in which the elution amount of the Ni ion is decreased as far as possible is proposed as the stainless steel for avoiding the metal allergy (see PTL 1).

According to this proposal, on the assumption that it is able to cope with a lot of applications as described above, in order to realize a stainless steel in which the Ni content in the stainless steel is decreased to an extent that Ni is not substantially contained, and at the same time, not only excellent corrosion resistance, durability, strength and toughness, but also excellent formability and wear resistance are exhibited, a chemical component composition is restricted.

A basic chemical component composition of the stainless steel according to this proposal is restricted so as to contain, as a chemical component composition (% by mass), $0<C$ (carbon)$\leq 0.08$, $0 \leq Si$ (silicon)$<0.50$, $0 \leq Mn$ (manganese)$\leq 1.50$, $15 \leq Cr$ (chromium)$\leq 30$, $0 \leq Ni<0.05$, $1 \leq Mo$ (molybdenum)$\leq 10$, $1.00<N$ (nitrogen)$\leq 2.00$, and $0 \leq Ca$ (calcium)$<0.005$, with the remainder being Fe (iron) and inevitable impurities.

In a usual austenite-based stainless steel, Fe, Cr, Ni, and Mo are essential chemical composition components, and Ni bears an important role as an austenite forming element. However, the above-described proposal is constructed in such a manner that the role of Ni in the conventional austenite-based stainless steel is complemented by other chemical composition component.

In particular, N (nitrogen) carries out an important role as a complementary component of Ni. N is an austenite forming element and is a constituent component which also contributes to an enhancement of the strength.

However, if a large amount of N is contained, the formation of Cr nitride is promoted, and the corrosion resistance is lowered by a reduction of a Cr oxide film to be caused due to a lowering of the Cr content. In addition, in particular, in the bio-environment where various ions such as a Cl (chlorine) ion, etc. are present, there are involved such problems that the corrosion resistance is conspicuously lowered and that the toughness is also lowered.

Furthermore, in the case of an austenite-based stainless steel having more than 1% by mass of N blended therein as in the above-described proposal, there is involved such a problem that the hardness becomes high due to solid-solution strengthening with N, so that the workability and moldability are deteriorated.

In view of such circumstances, the development of a stainless steel which does not substantially contain Ni, controls the content of N as far as possible, has a metal allergy onset-preventing effect, and is excellent in terms of workability and moldability and the development of a stent for vasodilatation using such a stainless steel were earnestly desired.

CITATION LIST

Patent Literature

[PTL 1] JP-A-2007-51368

SUMMARY OF INVENTION

Technical Problem

In view of the foregoing background, the present invention has been made, and an object thereof is to provide a nickel-free stainless steel stent using a stainless steel which does not substantially contain Ni in the stainless steel, has a metal allergy onset-preventing effect, and is excellent in terms of precision workability, strength, and ductility.

Solution to Problem

Specifically, the nickel-free stainless steel stent according to the present invention has the following characteristic features.

(1) A nickel-free stainless steel stent using a stainless steel containing, as a chemical composition, from 15 to 30% by mass of Cr, from 0.97 to 2% by mass of Mo, and from 0.5 to 1% by mass of N, with the remainder being Fe, and optionally containing inevitable impurities.

(2) A nickel-free stainless steel stent using a stainless steel containing, in addition to the chemical composition as set forth above in (1), from 0 to 0.50% by mass of Si, from 0.01 to 0.20% by mass of Mn, from 0 to 0.01% by mass of P, and from 0 to 0.1% by mass of Al.

(3) A nickel-free stainless steel stent using a stainless steel containing, in addition to the chemical composition as set forth above in any one of (1) or (2), from 0 to 0.5% by mass of Ti, from 0 to 0.5% by mass of Nb, and from 0 to 0.005% by mass of B.

Advantageous Effects of Invention

According to the invention as set forth above in (1), since the nickel-free stainless steel stent is formed using a stainless steel having, as a chemical composition, the specified contents of Cr, Mo, and N, with the remainder being Fe, and optionally containing inevitable impurities, a nickel-free stainless steel stent which has a metal allergy onset-preventing effect and which is excellent in terms of precision workability, strength, and ductility can be provided.

According to the invention as set forth above in (2) or (3), since the nickel-free stainless steel stent is formed using a stainless steel having, in addition to the chemical composition of the stainless steel of the invention as set forth above in (1), the specified contents of Si, Mn, P, and Al, and the specified contents of Ti, Nb, and B, a nickel-free stainless steel stent in which the effects of the invention as set forth above in (1) are more surely made conspicuous can be provided.

DESCRIPTION OF EMBODIMENTS

Modes for carrying out the present invention are hereunder described. As a matter of course, the following description is made for the purpose of enabling one to understand the gist of the invention more distinctly, and it should not be construed that the present invention is limited thereto.

The stainless steel used for the nickel-free stainless steel stent according to the invention (hereinafter abbreviated simply as "stent") is a stainless steel which does not substantially contain Ni and which contains, as essential components, Cr, Mo, and N in specified proportions as well as Fe.

<Cr (Chromium)>

Cr that is an essential component of the stainless steel used in the present invention is an important constituent element for imparting corrosion resistance to the stainless steel, and in particular, it is an important component for realizing the suppression of local corrosion resistance in the corrosion environment with body fluids containing a Cl ion of sodium chloride, etc., or the like.

In the stainless steel of the present invention, the content of Cr is in the range of from 15 to 30% by mass, and preferably from 20 to 25% by mass. By regulating the content of Cr to this range, a stainless steel which is excellent in terms of ductillity and reduction of area in a state where the strength is sufficiently ensured can be provided.

When the content of Cr exceeds 30% by mass, in view of the fact that Cr is also a ferrite forming element, an intermetallic compound is liable to deposit, and as a result, there is a concern that embrittlement of the steel is caused. In addition, when the content of Cr is less than 15% by mass, there may be the case where sufficient corrosion resistance and strength are not obtained.

<Mo (Molybdenum)>

Mo that is an essential component of the stainless steel used in the present invention is an element which enhances the corrosion resistance of the stainless steel.

In the stainless steel of the present invention, the content of Mo is in the range of from 0.97 to 2% by mass, and preferably from 0.97 to 1.05% by mass.

When the content of Mo is less than 0.97% by mass, there is a possibility that the effects cannot be sufficiently exhibited.

<N (Nitrogen)>

N that is an essential component of the stainless steel used in the present invention is an effective component such that N in a solid-solution state enhances the corrosion resistance in the corrosion environment with body fluids containing a Cl ion of sodium chloride, etc., or the like. In particular, in the present invention, N also bears an extremely significant role as a measure for ensuring the austenite forming elements.

In the stainless steel of the present invention, the content of N is in the range of from 0.5 to 1.0% by mass, and preferably from 0.8 to 0.97% by mass. By regulating the content of N to this range, a stainless steel which is able to contrive to stabilize the austenite crystal structure and which is excellent in terms of strength and plastic workability can be provided.

When the content of N exceeds 1.0% by mass, the formation of Cr nitride is liable to be promoted, and there is a concern that the workability is also lowered.

When the content of N is less than 0.5% by mass, an austenite single phase is not formed, but a two-phase stainless steel is formed, and there is a concern that the corrosion resistance and strength are lowered.

In the present invention, it is preferable that not only each of the contents of Cr, Mo, and N falls within each of the foregoing ranges, but the corrosion resistance equivalent (PRE) represented by the following formula (1) satisfies the following formulae (2) and (3).

$$\text{PRE} = (\text{Cr content}) + (\text{Mo content}) \times 3 + (\text{N content}) \times 10 \quad (1)$$

$$\text{PRE} > 150 \times A \quad (2)$$

$$\text{PRE} > 3.5 \times D \quad (3)$$

In the formula (2), $A$ represents an area occupancy (%) of a nonmetallic inclusion in the steel; and in the formula (3), $D$ represents a maximum diameter ($\mu$m) of nonmetallic inclusions in the steel.

The relation of the corrosion resistance equivalent (PRE) with the area occupancy ($A$) (%) of a nonmetallic inclusion in the steel and the maximum diameter ($D$) ($\mu$m) of a nonmetallic inclusion in the steel is described below in detail.

Since a stainless steel forms a firm passivation film on the steel surface, even under the environmental conditions under which the stainless steel is used as a biocompatible material or the like, it exhibits the corrosion resistance and suppresses the elution of a metal. However, when a nonmetallic inclusion such as an oxide, a sulfide, etc. is present in the steel, this nonmetallic inclusion becomes a film defect of the steel and causes deterioration of the corrosion resistance, and even under the use environment as a biocompatible material or the like, it causes the elution of a metal. A degree of this deterioration in corrosion resistance or the like depends upon the corrosion resistance equivalent (PRE) prescribed by the above-described formula (1), the area occupancy (A) (%) of a nonmetallic inclusion in the steel, and the maximum diameter (D) (μm) of a nonmetallic inclusion in the steel (provided that in the case where a major axis and a minor axis are present, a maximum diameter of the major axis is defined as D).

In order to realize the satisfactory suppression of local corrosion resistance of the stainless steel in the corrosion environment with body fluids containing a Cl ion of sodium chloride, etc., or the like, it is preferable that both the foregoing equations (2) and (3) are satisfied.

Here, as for the measuring method of the area occupancy (A) (%) of a nonmetallic inclusion in the steel, the area occupancy (A) (%) can be, for example, determined by polishing a cross section parallel to the forging or rolling direction to a mirror surface, measuring the maximum diameter (D) (μm) of a nonmetallic inclusion in the steel in the field of view in 150 fields of view using an optical microscope of 1,000 magnifications, and measuring its image by means of image analysis.

In addition, in the stainless steel used in the present invention, it is desirable to control, in addition to the above-described essential chemical composition components, the contents of Si, Mn, P, and Al.

<Si (Silicon)>

Si is an element which acts as a deoxidizing agent. In the stainless steel of the present invention, when Si is contained, $SiO_2$ that is a deoxidation product is formed, and the growth of a nonmetallic inclusion is promoted. Also, there is a concern that a lowering of the corrosion resistance is caused, and the formation of a δ-ferrite phase exhibiting magnetism is promoted. Therefore, from these standpoints, it is preferable to control the content of Si at a low level.

Incidentally, in the present invention, N is contained in a specified range as described above. Therefore, in a melting step of a stainless steel by means of a pressurized ESR process (pressurized electro-slag remelting) as described later, an additional source material containing Si, such as silicon nitride, etc. is not used as an N additional source; but, a ferrochrome nitride alloy, chromium nitride, or the like is used, a maximum pressure of a nitrogen gas in the melting and refining atmosphere is controlled, and an Al single system is used as an additional slag component.

According to this, the separation of the nonmetallic inclusion from a molten metal into a slag is promoted, and a contamination source of Si into the molten metal is controlled, whereby it becomes possible to make the control of the Si content effective.

On the assumption that the foregoing melting step is used, the Si content in the stainless steel of the present invention can be regulated to the range of from 0 to 0.5% by mass, and preferably 0.11 to 0.16% by mass.

<Mn (Manganese)>

Similar to Si, Mn is an element acting as a deoxidizing agent and contributes to stabilization of an austenite phase. Furthermore, Mn has an effect for increasing the solubility of N in the molten metal, and therefore, Mn is an extremely effective element in the case where it is intended to produce an N-containing stainless steel.

In the present invention in which it is essential to contain N, from this viewpoint, it is extremely effective to contain Mn. However, when the content of Mn is increased, in conformity with the case of an increase of the Si content, MnO that is a deoxidation product has an action to promote the growth of an oxide-based inclusion, and therefore, there is a possibility that not only the corrosion resistance of the steel is lowered, but the toughness is lowered.

Then, similar to Si, so far as a deoxidation action of Mn is concerned, for the purpose of ensuring the deoxidation ability even when its addition amount is restricted, by adding an appropriate amount of Al, it is possible to decrease the amount of dissolved oxygen in the molten metal to an extremely low value. In addition, desirably, the deoxidation effect is further expressed by means of complex deoxidation due to additional addition of Ce thereto, thereby enabling the oxide-based inclusion to decrease.

By adopting the deoxidation method as thus controlled, it becomes possible to further decrease the content of Mn which originally has the deoxidation function.

From these viewpoints, in the present invention, the content of Mn is in the range of from 0.01 to 0.20% by mass, and preferably from 0.01 to 0.12% by mass. By regulating the content of Mn to this range, the amount of a nonmetallic inclusion containing an Mn-based oxide can be decreased. Thus, such is extremely effective for enhancing the corrosion resistance of the stainless steel of the present invention.

In the present invention, from the above-described viewpoint of improving the corrosion resistance and toughness, similar to the case in the Si content, even when the Mn content is regulated to 0% by mass, sufficient deoxidation can be achieved by performing dissolution and refining in an N atmosphere under a prescribed pressure by adopting the pressurized ESR process to adequately perform the deoxidation operation. In addition, even by the addition of an adequate amount of Al and deoxidation, not only sufficient deoxidation can be achieved, but the formation of an $Al_2O_3$-containing inclusion is suppressed, thereby enabling the residual amount to decrease extremely.

<P (Phosphorus)>

P is an element which is inevitably incorporated in the melting step of the stainless steel. It is desirable that the content of P is low as far as possible because it segregates in a grain boundary to easily cause a lowering of the corrosion resistance, and there is a concern that a lowering of the toughness is caused. For that reason, the content of P in the present invention is regulated in the range of from 0 to 0.01% by mass.

Then, the stainless steel used in the present invention can contain, in addition to the above-described components, Ti (titanium), niobium (Nb), and B (boron).

In the present invention, the content of Ti is in the range of from 0 to 0.5% by mass, and preferably from 0 to 0.2% by mass; the content of Nb is in the range of from 0 to 2% by mass, and preferably from 0 to 0.2% by mass; and the content of B is in the range of from 0 to 0.05% by mass, and preferably from 0 to 0.005% by mass.

By regulating the contents of Ti, Nb, and B to the foregoing ranges, respectively, a crystal grain refining effect can be exhibited together with the formation of a nitride. Then, according to this, it becomes possible to enhance the ductillity along with the strength. Though these properties may be conventionally regarded as reciprocal to each other, by regulating the contents of Ti, Nb, and B to the foregoing ranges, it becomes possible to make the both compatible to each other.

<Al (Aluminum)>

In the present invention, at the time of melting of an ESR steel ingot, in order to ensure the cleaning properties of an oxide-based nonmetallic inclusion of the ESR steel ingot at a high level as far as possible through the deoxidation of a molten metal, it is desirable to avoid the complex deoxidation by Al as far as possible. It is preferable to leave the content of Al at a degree of incorporation by tolerance of the Al residual amount necessary at a melting stage in a consumable base electrode production stage. From such a viewpoint, the Al content in the ESR steel ingot desirably falls within the range of from 0 to 0.10% by mass, and preferably from 0.0024 to 0.0034% by mass.

Furthermore, in the present invention, it is desirable to control the contents of other components than those described above, for example, C (carbon), S (sulfur), and oxygen (O). (EN)<C (Carbon)>

C contributes to an enhancement of the strength of steel and is also effective as an austenite phase forming element. However, C is an element which when the content of C is in excess, impairs the corrosion resistance and toughness of the stainless steel. Thus, on the assumption of insurance of the strength and insurance of the austenite phase by other components, from the viewpoint of ensuring the corrosion resistance and toughness, it is desirable to decrease the content of C as far as possible.

From these standpoints, in the present invention, the content of C is preferably in the range of from 0 to 0.025% by mass, and preferably from 0.008 to 0.023% by mass.

<S (Sulfur)>

S is an element which is inevitably incorporated in the melting step of the stainless steel. For the purpose of suppressing the amount of MnS formed, it is desirable that the content of S is controlled as far as possible while regulating the content of Mn at a low level as far as possible. In the present invention, it is preferable to regulate the S content to the range of from 0 to 0.002% by mass.

<O (Oxygen)>

O is an element which is inevitably incorporated in the melting step of the steel, and it is desirable that its content is low as far as possible. From such a viewpoint, in the present invention, it is preferable to regulate the content of O to the range of from 0 to 0.003% by mass.

Furthermore, in the present invention, it is also considered to contain W (tungsten), V (vanadium), and Ce (cerium).

<W (Tungsten) and V (Vanadium)>

W is an element enhancing the corrosion resistance of the stainless steel. However, similar to Cr, W is an element which when its content is in excess, forms a ferrite. Therefore, the formation of an intermetallic compound becomes conspicuous, thereby possibly causing embrittlement of the steel. In consequence, the content of W is preferably in the range of from 1 to 10% by mass.

On the other hand, V is an element which is effective for enhancing the local corrosion resistance in the corrosion environment with body fluids containing a Cl ion of sodium chloride, etc., or the like. However, when its content is in excess, the hot workability of the stainless steel is inhibited. In consequence, it is preferable to regulate the content of V to the range of from 1 to 10% by mass.

By containing one or more of W and V within the foregoing content ranges, the corrosion resistance of the stainless steel can be enhanced.

<Ce (Cerium)>

Ce is effective as a deoxidizing agent and a desulfurizing agent. In consequence, Ce contributes to a decrease of the nonmetallic inclusion and contributes to enhancements of the corrosion resistance and toughness.

In the present invention, the content of Ce is regulated to the range of from 0.01 to 0.10% by mass. By regulating the content of Ce to this range, the corrosion resistance and toughness of the stainless steel can be much more enhanced.

When the content of Ce is less than 0.01% by mass, the above-described effects cannot be sufficiently exhibited, whereas when Ce is contained in an amount exceeding 0.10% by mass, the hot workability of the stainless steel is inhibited, and hence, such is not preferable.

In the present invention, elements which have not been described above may be contained as inevitable impurities. For example, the same is applied to Ni (nickel). It is important that Ni is not substantially contained.

The respective components constituting the stainless steel as described above are subjected to melting by the pressurized ESR process that is an efficient melting process for the purpose of satisfying the characteristic features of the chemical component composition. The melting process by the known pressurized ESR process which is suitable for melting the stainless steel of the present invention is hereunder described.

In the pressurized ESR process for melting the stainless steel of the present invention, an ESR steel ingot can be melted using an apparatus in which the pressure of an $N_2$ gas atmosphere in the dissolution and refining period can be adjusted within the range of from about 0.1 to 5 MPa.

Here, a desired ESR steel ingot can be melted by using a nitrogen-added consumable electrode as a consumable electrode and further using, as a slag, a premelting slag of calcium fluoride ($CaF_2$) or calcium oxide (CaO) and performing redissolution and refining using the above-described nitrogen-added consumable electrode as a dissolution raw material.

On that occasion, in order to regulate the N content of the ESR steel ingot to a target value, the basic operation of the adjustment can be performed by (1) keeping the symmetry of the content of N contained in a nitrogen-added material fixed in the surface layer part of the above-described nitrogen-added consumable electrode and the distribution of the nitrogen-added material of the electrode surface layer part, (2) controlling the pressure of the $N_2$ gas atmosphere in the dissolution and refining period, and (3) controlling the dissolution and refining temperature.

The basic technique of melting of a highly clean steel is based on strong deoxidation mainly with metallic Al of the molten metal, and more desirably, complex deoxidation added with an appropriate amount of metallic Ce is also adopted. Incidentally, the addition of Al is made by inserting and installing a metallic Al wire in the consumable electrode. Furthermore, with respect to the component composition of the molten slag, by taking into consideration extreme lowering of potentials of oxygen and sulfur of the slag and optimization of the fluidity, it is possible to contrive to promote flotation or separation removal of deoxidation product and desulfurization product from a molten metal (molten steel) bulk or molten droplet into a molten slag phase and to prevent the reoxidation of the molten metal bulk.

The ESR steel ingot melted by the pressurized ESR process in this way can be processed into a linear form suited for the stent according to the present invention by adopting one or more processing technologies selected from the group of hot rolling, hot forging, hot extrusion, cold rolling, cold drawing, clod drawing, and the like.

As a method for producing the stent according to the present invention from the stainless steel of the thus processed linear material, the conventional technologies for producing a stent using, as a material, the conventional austenite-based stainless steel, for example, SUS316L, etc., can be adopted.

As for these technologies of producing a stent, the stent can be produced by processing a stainless steel in a linear form and knitting it in a net form. Such a stent in a net form is inserted in a state of being thinly folded into a diseased part of a blood vessel by a catheter and then swollen by a balloon to expand the net, thereby widening the blood vessel.

Figure 1:
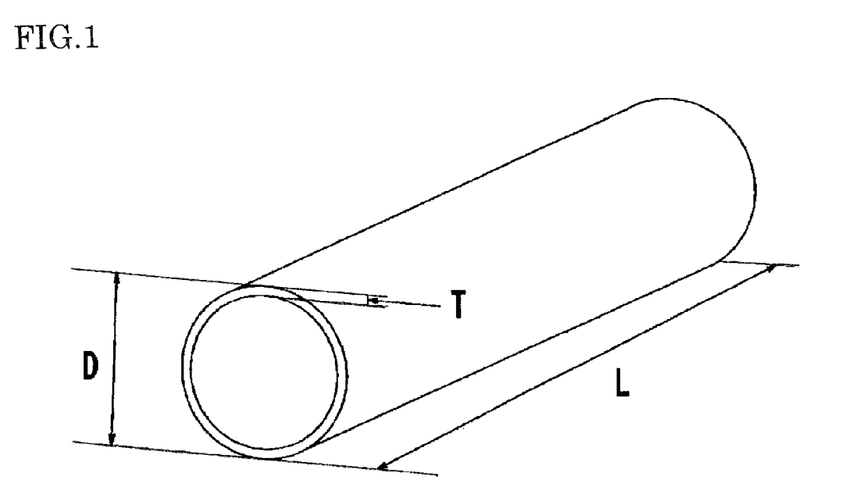
FIG. 1 is a diagrammatic view expressing the shape of a tubular stainless steel stent according to the present invention.

In addition, the stent can also be prepared by perforating a cross-sectional center of a stainless steel molded in a rod-like form in the longitudinal direction by means of mechanical processing to fabricate a pipe, subjecting it to clod drawing processing, and further fabricating a thin pipe in a final shape shown in FIG. 1, followed by applying laser processing to form a prescribed pattern.

A diagrammatic view of a tubular stent having been subjected to clod drawing processing is shown in FIG. 1. In the present invention, as shown in FIG. 1, by forming the stent in a tubular shape having an outer diameter (D) of 1.4 mm, a tube wall thickness (T) of from 0.1 to 0.15 mm, and a length (L) of from 10 to 20 mm, it can be suitably used as a stent for coronary artery.

Next, the present invention is specifically described on the basis of the following Examples. As a matter of course, it should be construed that the present invention is not limited at all by these Examples.

EXAMPLES

Evaluation of Elution of Nickel Ion

Nickel-free stainless steels (23Cr-1Mo-1N) of Examples 1 to 6 and a stainless steel (SUS316L) of Comparative Example 1, each having a chemical composition shown in Table 1 (the numerical values express % by mass), were each formed into a shape having a diameter of 10 mm and a thickness of 1 mm and subjected to ultrasonic cleaning in acetone, followed by autoclave sterilization. Every one sample was put in 1 mL of a culture solution ((endothelial cell basal medium)+(endothelial cell addition factor) (EGM-2 Bullet Kit, Sanko Junyaku Co., Ltd., Cat. #CC-3162)) and incubated under a condition at 37° C. for 24 hours.

Three samples of each of Examples 1 to 6 and Comparative Example 1 were gathered in one, and the elution amount of a nickel ion in the culture solution was quantitatively determined by an ICP emission spectral analyzer (available from Nippon Jarrell-Ash Co. Ltd.).

The results are shown in Table 2. As noted from the results shown in Table 2, in the case of the nickel-free stainless steel, the elution of a nickel ion was not observed, whereas in the case of SUS316L stainless steel, the elution of a nickel ion was observed.

<Verification of Restenosis Rate>

Each of a nickel-free stainless steel stent (23Cr-1 Mo-1N: Example 1) and a stainless steel stent (SUS316L: Comparative Example 1) having a length of 10 mm was fabricated from a seamless pipe having an outer diameter of 1.4 mm and a wall thickness of 0.1 mm. The fabricated stent was mounted on a catheter and then sterilized with an ethylene oxide gas. Thereafter, a three-month-old pig (body weight: about 60 kg) under anesthesia was indwelled with the stent by the catheter in a left anterior descending coronary artery (LAD), a left circumflex coronary artery (LCX), or a right coronary artery (RCA). The number of the stents indwelled in the LAD, LCX, or RCA was 2 at maximum. Four weeks after indwelling, the stenosis rate was evaluated in terms of a blood vessel diameter by means of contrast imaging in conformity with the classification of AHA (American Heart Association) of coronary artery.

Figure 2:
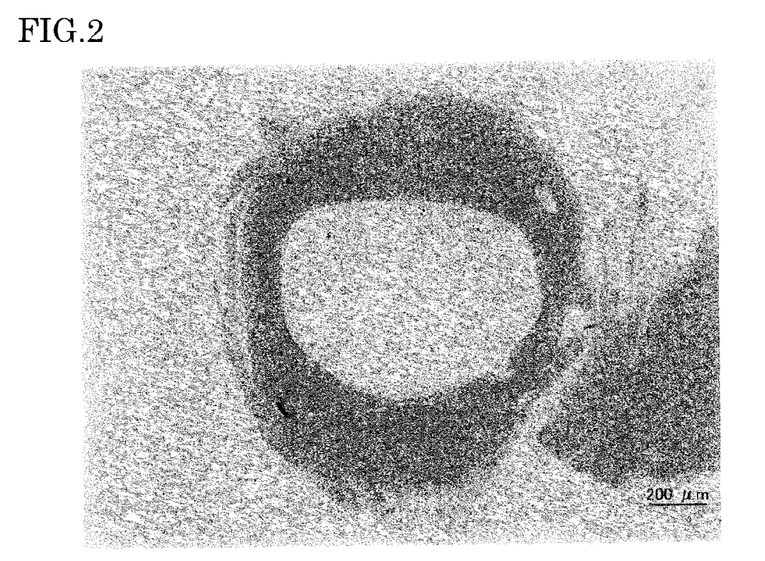
FIG. 2 is a pathological photograph of a blood vessel four weeks after implantation of a nickel-free stainless steel stent.
Figure 3:
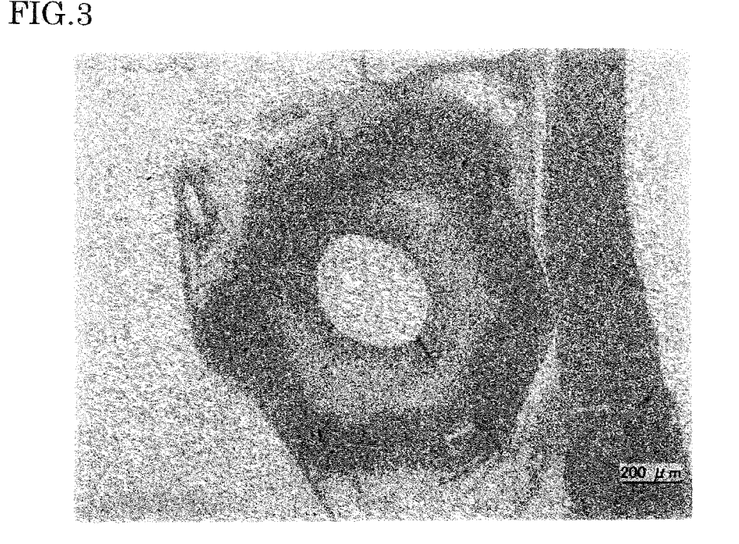
FIG. 3 is a pathological photograph of a blood vessel four weeks after implantation of an SUS316L stent.

A pathological photograph of the blood vessel four weeks after indwelling of the stainless steel stent of Example 1 is shown in FIG. 2; and a pathological photograph of the blood vessel four weeks after indwelling of the SUS316L-made stent of Comparative Example 1 is shown in FIG. 3.

The restenosis rate was defined as 0% in the case of no restenosis; 25% in the case of from 1 to 25%; 50% in the case of from 25 to 50%; 75% in the case of from 51 to 75%; 90% in the case of from 75 to 99% (without a delay of the flow of contrast medium in the stenosis part); 99% in the case of from 75 to 99% (with a delay of the flow of contrast medium in the stenosis part); and 100% in the case of complete stenosis, respectively. The case where the restenosis rate was not more than 25% was considered to be effective.

The results are shown in Table 3. As noted from the results of Table 3, in the nickel-free stainless steel stent of Example 1, a proportion of the samples in which the effects were observed reached 80%, whereas in the conventional SUS316L-made stent of Comparative Example 1, a proportion of the samples in which the effects were observed was only 20%.

TABLE 1

|  |  | Ni | Cr | Mo | N | Si | Mn | P | Ti | Nb | B | C | S | Al | O | Fe |
|---|---|---|---|---|---|---|---|---|---|---|---|---|---|---|---|---|
| Example 1 | 23Cr—1Mo— | 0.032 | 20.1 | 1.05 | 0.84 | 0.12 | 0.12 | 0.005 | — | — | — | 0.019 | — | 0.0024 | 0.0024 | Bal. |
| Example 2 | 1N | 0.004 | 22.93 | 1.05 | 0.97 | 0.11 | 0.08 | <0.003 | — | — | — | 0.022 | — | 0.0034 | 0.0034 | Bal. |
| Example 3 |  | 0.01 | 22.73 | 0.98 | 0.93 | 0.14 | 0.01 | <0.005 | — | — | — | 0.008 | — | 0.0026 | 0.0026 | Bal. |
| Example 4 |  | 0.04 | 22.73 | 1.00 | 0.95 | 0.16 | 0.10 | 0.003 | — | — | 0.0017 | 0.023 | 0.019 | — | — | Bal. |
| Example 5 |  | 0.04 | 22.78 | 1.00 | 0.90 | 0.15 | 0.10 | 0.003 | 0.15 | 1.00 | — | 0.019 | — | — | — | Bal. |
| Example 6 |  | 0.041 | 23.41 | 0.97 | 0.93 | 0.14 | 0.10 | <0.005 | 0.11 | — | — | 0.020 | — | — | — | Bal. |
| Comparative Example 1 | SUS316L | 11.87 | 16.72 | 2.01 | 0.021 | 0.48 | 1.50 | 0.027 | — | — | — | 0.025 | 0.002 | 0.0042 | 0.0042 | Bal. |

TABLE 2

|  |  | Concentration of Ni ion eluted (µg/mL) |
|---|---|---|
| Examples 1 to 6 | 23Cr—1Mo—1N | <0.01 |
| Comparative Example 1 | SUS316L | 0.03 |

TABLE 3

|  |  |  | Restenosis rate (%) | Proportion of samples with effects (%) |
|---|---|---|---|---|
| Example 1 | 23Cr—1Mo—1N | First sample | 25 | 80 |
|  |  | Second sample | 25 |  |
|  |  | Third sample | 75 |  |

TABLE 3-continued

|  |  |  | Restenosis rate (%) | Proportion of samples with effects (%) |
|---|---|---|---|---|
|  |  | Fourth sample | 25 |  |
|  |  | Fifth sample | 25 |  |
| Comparative Example 1 | SUS316L | First sample | 75 | 20 |
|  |  | Second sample | 75 |  |
|  |  | Third sample | 90 |  |
|  |  | Fourth sample | 50 |  |
|  |  | Fifth sample | 25 |  |

It was confirmed from the foregoing results that as compared with the conventional stainless steel stent, the nickel-free stainless steel stent according to the present invention is substantially free from the elution of nickel, has a low restenosis rate, and suppresses the onset of a disease of metal allergy.

<Relation of Nitrogen Content with Workability>

Figure 4:
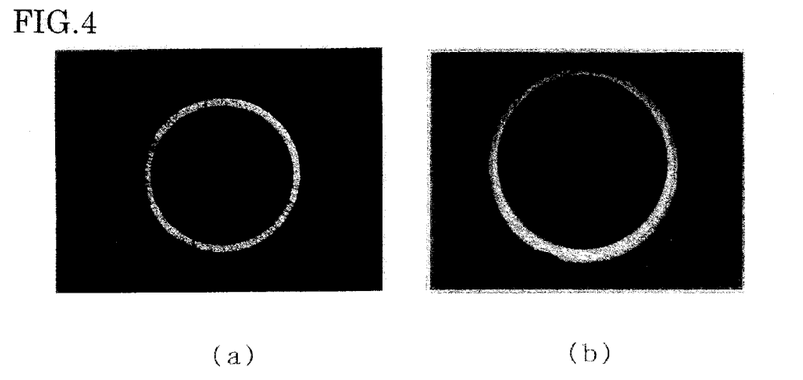
FIG. 4 is a comparative photograph in workability between (a) a nickel-free stainless steel stent having a nitrogen content of less than 1% by mass and (b) a stainless steel stent having a nitrogen content of 1% by mass or more.

With respect to the nickel-free stainless steel stent having a nitrogen content of less than 1% by mass and the stainless steel stent having a nitrogen content of 1% by mass or more, the relation of the nitrogen content with the workability was confirmed. A cross-sectional photograph of each of the stents is shown in FIG. 4.

In the nickel-free stainless steel stent (a) having a nitrogen content of less than 1% by mass, it was confirmed that following a decrease of the nitrogen content, the hardness is lowered, the workability becomes improved, and a thin pipe having a uniform wall thickness can be formed. On the other hand, in the stainless steel stent (b) having a nitrogen content of 1% by mass or more, it was confirmed that the workability is lowered. and the wall thickness becomes nonuniform.

From the foregoing results, the excellent workability of the nickel-free stainless steel stent having a nitrogen content of less than 1% by mass was confirmed.

<Evaluation of Cell Adhesion and Proliferation Properties>

Each of stainless steel samples (diameter: 10 mm) shown in the following Table 4 was prepared, and human umbilical vein endothelial cells (HUVEC) were seeded on the surface thereof. Thereafter, the cell adhesion and proliferation properties were evaluated at the points of time of 3 hours, 1 day, and 3 days.

Figure 5:
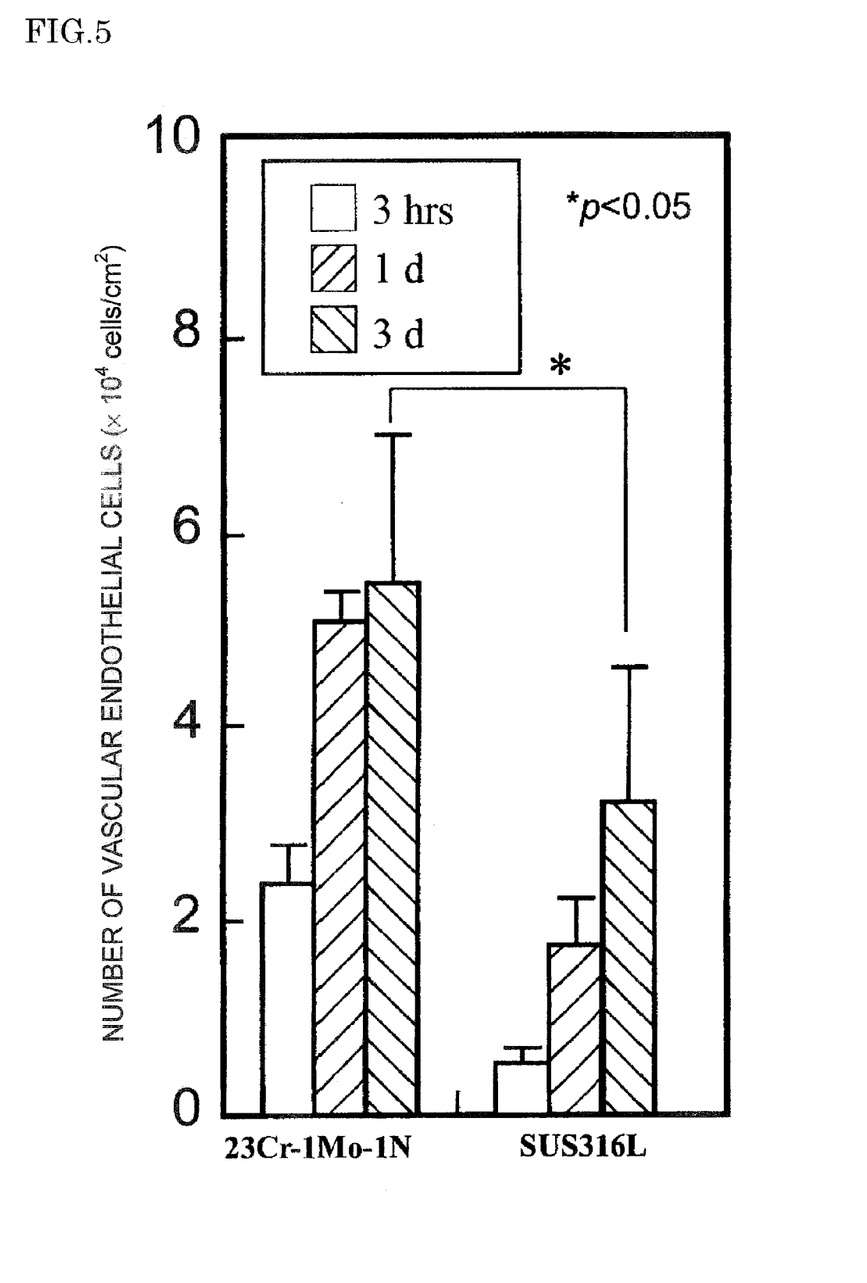
FIG. 5 is a graph showing a change of the number of vascular endothelial cells at the points of time of 3 hours, 1 day, and 3 days.
Figure 6:
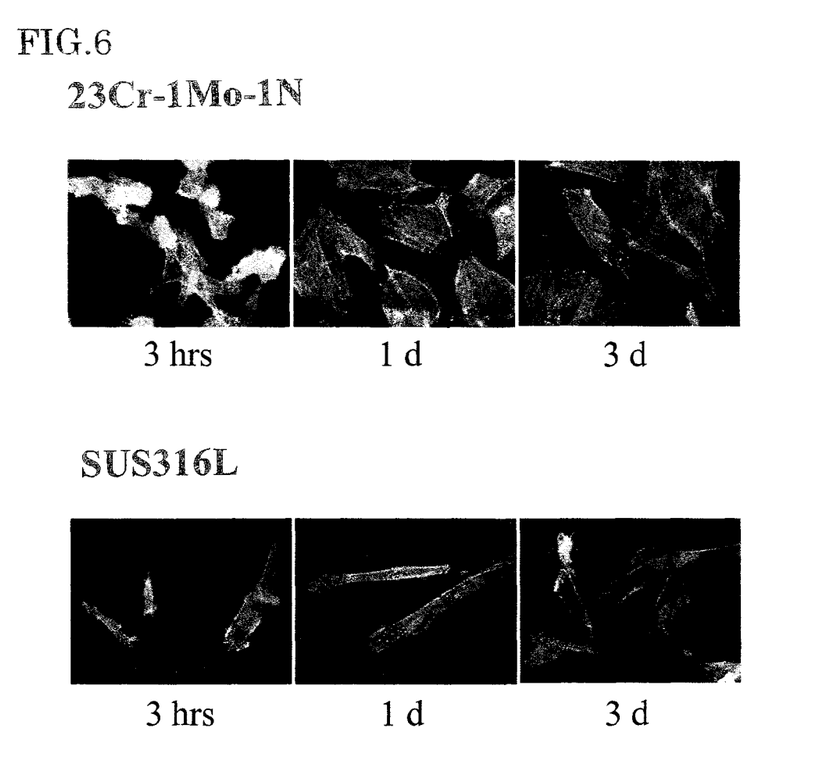
FIG. 6 is a fluorescence observation photograph in which proliferation properties of cells at the points of time of 3 hours, 1 day, and 3 days were confirmed.

The evaluation was made by the measurement of the number of cells with WST-8 and fluorescence observation. The results of a change of the number of vascular endothelial cells are shown in FIG. 5, and a fluorescence observation photograph regarding the proliferation properties of cells is shown in FIG. 6.

TABLE 4

| Example 1 | 23Cr—1Mo—1N irradiated with UV (for 2 hours) |
| Comparative Example 1 | SUS316L irradiated with UV (for 2 hours) |

Cell passage number: 5
Cell seeding density: 2,500 cells/500 μL (using a 48-well plate)
N number: 5

It was confirmed from the results of FIGS. 5 and 6 that as compared with SUS316 containing nickel, the nickel-free high-nitrogen stainless steel (23Cr-1 Mo-1N) of the present invention exhibits significantly high cell adhesion and proliferation properties.

The invention claimed is:

1. A nickel-free stainless steel stent, comprising a stainless steel containing, as a chemical composition,
    from 15 to 30% by mass of Cr,
    from 0.97 to 2% by mass of Mo,
    from 0.8 to 1% by mass of N,
    from 0.01 to 0.20% by mass of Mn, and
    from 0.0024 to 0.0034% by mass of Al,
    with the remainder being Fe, and optionally containing inevitable impurities.

2. The nickel-free stainless steel stent according to claim 1, wherein the stainless steel further contains,
    from 0.11 to 0.16% by mass of Si, and
    from 0 to 0.01% by mass of P.

3. The nickel-free stainless steel stent according to claim 1, wherein the stainless steel further contains,
    from 0 to 0.5% by mass of Ti,
    from 0 to 2% by mass of Nb, and
    from 0 to 0.05% by mass of B.

4. A method for producing a stainless steel for a nickel-free stainless steel stent according to claim 1, characterized by performing melting by regulating the pressure of an $N_2$ gas atmosphere in the dissolution and refining period within the range of from 0.1 to 5 MPa by the pressurized ESR process.

5. The method for producing a stainless steel for a nickel-free stainless steel stent according to claim 4, characterized by using a nitrogen-added consumable electrode as a consumable electrode.

6. The method for producing a stainless steel for a nickel-free stainless steel stent according to claim 4, characterized by using, as a slag, a premelting slag of calcium fluoride or calcium oxide.

7. The method for producing a stainless steel for a nickel-free stainless steel stent according to claim 4, characterized by performing deoxidation by the addition of aluminum.

8. A method for producing a nickel-free stainless steel stent, characterized by processing the stainless steel produced by the method according to claim 4 in a rod-like or linear form and subsequently processing it into a prescribed stent shape.

9. The stainless steel for a nickel-free stainless steel stent according to claim 1, wherein when a test piece formed in a shape having a diameter of 10 mm and a thickness of 1 mm is subjected to ultrasonic cleaning in acetone and then autoclave sterilization, and every one sample is put in 1 mL of a culture solution comprising endothelial cell basal medium+endothelial cell addition factor (EGM-2 Bullet Kit, Sanko Junyaku Co., Ltd., Cat.# CC-3162), and incubated under a condition at 37° C. for 24 hours, an elution amount of a nickel ion in ICP emission spectral analysis is less than 0.01 μg/mL.

10. The nickel-free stainless steel stent according to claim 1, wherein
    when a stent sample having a length of 10 mm from a seamless pipe having an outer diameter of 1.4 mm and a wall thickness of 0.1 mm is mounted on a catheter and then sterilized with an ethylene oxide gas; a three-month-old pig (body weight: about 60 kg) under anesthesia is indwelled with the stent sample in the number of 2 at maximum by the catheter in a left anterior descending coronary artery (LAD), a left circumflex coronary artery (LCX), or a right coronary artery (RCA); and four weeks after indwelling, a stenosis rate is evaluated in terms of a blood vessel diameter by contrast imaging in conformity with the classification of AHA (American Heart Association) of coronary artery, a proportion of the samples whose restenosis rate is not more than 25%, at which the effects are confirmed, is at least 80%.

11. The nickel-free stainless steel stent according to claim 2, wherein the stainless steel further contains,
from 0 to 0.5% by mass of Ti,
from 0 to 2% by mass of Nb, and
from 0 to 0.05% by mass of B.

12. A method for producing a stainless steel for a nickel-free stainless steel stent according to claim 2, characterized by performing melting by regulating the pressure of an $N_2$ gas atmosphere in the dissolution and refining period within the range of from 0.1 to 5 MPa by the pressurized ESR process.

13. A method for producing a stainless steel for a nickel-free stainless steel stent according to claim 3, characterized by performing melting by regulating the pressure of an $N_2$ gas atmosphere in the dissolution and refining period within the range of from 0.1 to 5 MPa by the pressurized ESR process.

14. A method for producing a stainless steel for a nickel-free stainless steel stent according to claim 11, characterized by performing melting by regulating the pressure of an $N_2$ gas atmosphere in the dissolution and refining period within the range of from 0.1 to 5 MPa by the pressurized ESR process.

15. The method for producing a stainless steel for a nickel-free stainless steel stent according to claim 12, characterized by using a nitrogen-added consumable electrode as a consumable electrode.

16. The method for producing a stainless steel for a nickel-free stainless steel stent according to claim 13, characterized by using a nitrogen-added consumable electrode as a consumable electrode.

17. The method for producing a stainless steel for a nickel-free stainless steel stent according to claim 14, characterized by using a nitrogen-added consumable electrode as a consumable electrode.

18. The method for producing a stainless steel for a nickel-free stainless steel stent according to claim 12, characterized by using, as a slag, a premelting slag of calcium fluoride or calcium oxide.

19. The method for producing a stainless steel for a nickel-free stainless steel stent according to claim 13, characterized by using, as a slag, a premelting slag of calcium fluoride or calcium oxide.

20. The method for producing a stainless steel for a nickel-free stainless steel stent according to claim 14, characterized by using, as a slag, a premelting slag of calcium fluoride or calcium oxide.

21. A nickel-free austenitic stainless steel stent, comprising a stainless steel containing, as a chemical composition,
from 20 to 25% by mass of Cr,
from 0.97 to 2% by mass of Mo,
from 0.8 to 1% by mass of N,
from 0.01 to 0.12% by mass of Mn and
from 0.0024 to 0.0034% by mass of Al,
with the remainder being Fe, and optionally containing inevitable impurities.

22. A nickel-free austenitic stainless steel stent, comprising a stainless steel containing, as a chemical composition,
from 22.73 to 23.41% by mass of Cr,
from 0.97 to 2% by mass of Mo,
from 0.8 to 1% by mass of N,
from 0.01 to 0.12% by mass of Mn, and
from 0.0024 to 0.0034% by mass of Al,
with the remainder being Fe, and optionally containing inevitable impurities.

* * * * *